(12) United States Patent
Hotier et al.

(10) Patent No.: US 6,177,604 B1
(45) Date of Patent: Jan. 23, 2001

(54) PROCESS FOR CO-PRODUCTION AND SEPARATION OF ETHYLBENZENE AND PARAXYLENE

(75) Inventors: Gerard Hotier, Rueil Malmaison; Fabio Alario, Neuilly sur Seine; Alain Methivier, Rueil Malmaison, all of (FR)

(73) Assignee: Institut Francais du Petrole (FR)

( * ) Notice: Under 35 U.S.C. 154(b), the term of this patent shall be extended for 0 days.

(21) Appl. No.: 09/219,392

(22) Filed: Dec. 23, 1998

(30) Foreign Application Priority Data

Dec. 26, 1997 (FR) .................................................. 97 16652

(51) Int. Cl.[7] ................................. C07C 7/12; C07C 7/00

(52) U.S. Cl. ........................... 585/805; 585/822; 585/825; 585/828

(58) Field of Search ................................... 585/805, 822, 585/825, 828

(56) References Cited

U.S. PATENT DOCUMENTS

| | | | |
|---|---|---|---|
| 5,244,650 | * 9/1993 | Kuznicki et al. | 423/718 |
| 5,284,992 | 2/1994 | Gerard et al. | 585/805 |
| 5,329,060 | 7/1994 | Swift | 585/805 |
| 5,629,467 | * 5/1997 | Hotier et al. | 585/805 |

* cited by examiner

Primary Examiner—Walter D. Griffin
Assistant Examiner—Tam M. Nguyen
(74) Attorney, Agent, or Firm—Millen, White, Zelano, & Branigan, P.C.

(57) ABSTRACT

Paraxylene and ethylbenzene are produced from an aromatic hydrocarbon feedstock by using adsorption zones in a simulated fluid bed. The feedstock is first passed into a first adsorption zone to produce a first paraxylene-rich fraction and a second ethylbenzene-rich fraction. The second fraction is then passed into a second adsorption zone to produce a third fraction containing essentially pure ethylbenzene and a fourth fraction containing a majority of orthoxylene and metaxylene. The fourth stream is then passed into an isomerization zone to produce an isomerate which is then recycled back to the first adsorption zone.

10 Claims, 1 Drawing Sheet

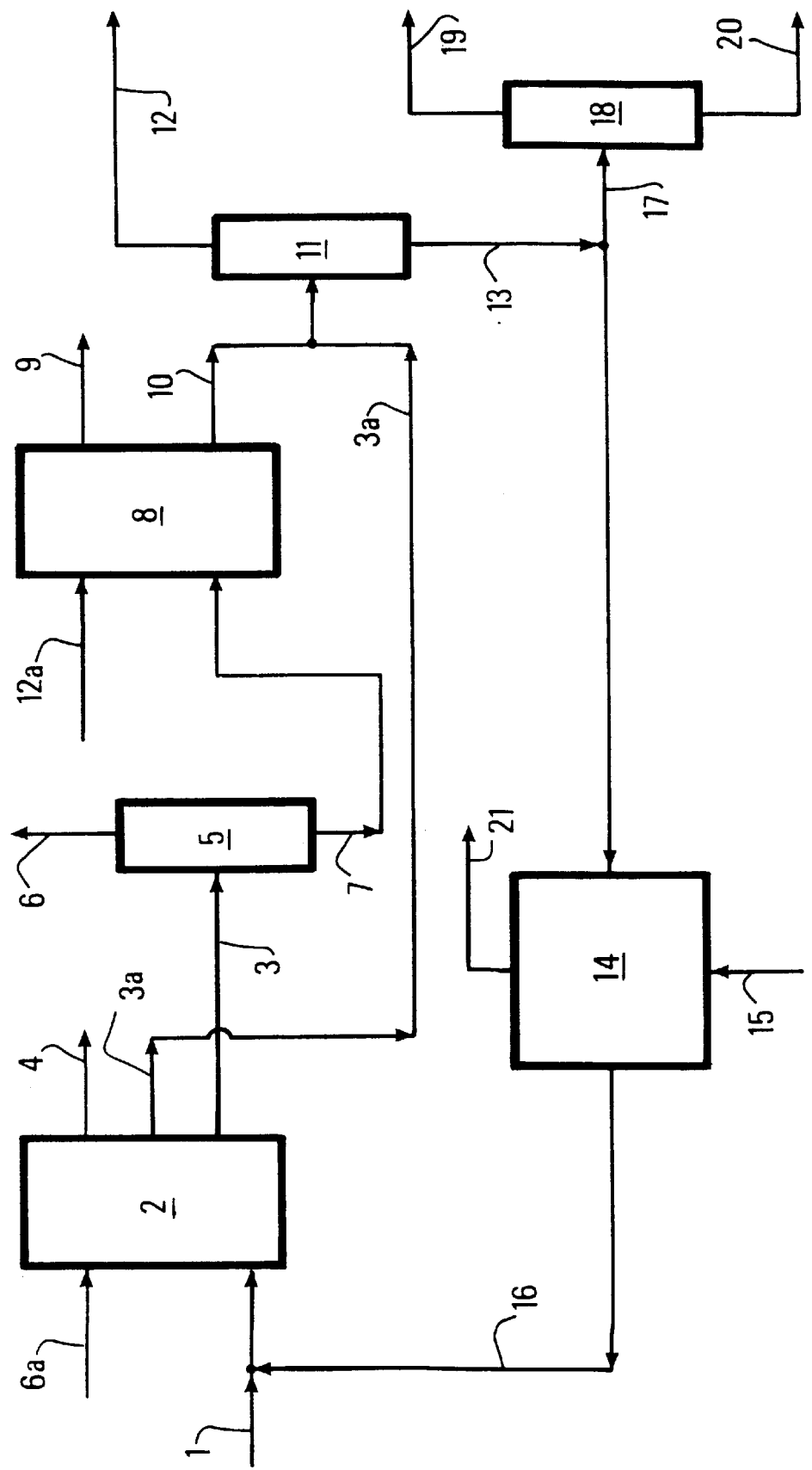

PROCESS FOR CO-PRODUCTION AND SEPARATION OF ETHYLBENZENE AND PARAXYLENE

The invention relates to a process for co-production of paraxylene and ethylbenzene from an aromatic hydrocarbon feedstock that contains isomers with 8 carbon atoms.

The invention applies particularly to the synthesis of very pure paraxylene for producing a petrochemical intermediate chemical, terephthalic acid.

BACKGROUND OF THE INVENTION

The production and separation of paraxylene are carried out in industrial practice by arranging the following in a loop:

a process for separation of the paraxylene by adsorption (U.S. Pat. Nos. 5,284,992; 5,401,476; and 5,329,060), whose effluents are paraxylene, on the one hand, and an aromatic $C_8$ petroleum fraction that is substantially free of paraxylene, on the other. Crystallization can be combined with the adsorption stage to obtain purer paraxylene (U.S. Pat. No. 5,284,992, U.S. Pat. No. 5,401,476, U.S. Pat. No. 5,329,060);

a process for isomerizing the aromatic $C_8$ petroleum fraction, whereby said process treats the second of the two effluents of the separation unit and produces an isomerate that contains paraxylene. This isomerate is recycled to the feedstock stream that feeds the paraxylene separation unit.

There are two classes of processes for isomerization of paraxylene: the first class is known by the term "converting isomerization" because ethylbenzene is in part converted into xylenes, which are in proportions that are close to those of the thermodynamic equilibrium. The catalysts that are used in the conversion isomerization steps are bifunctional. A zeolite, such as, for example, mordenite, ensures the conversion of orthoxylenes and metaxylenes into paraxylene by migration of the methyl groups. As a result, at the temperature in question, thermodynamic equilibrium is nearly reached among the three xylenes: at 400° C., typically, orthoxylene 24%, metaxylene 52%, and paraxylene 24%. Dispersed platinum ensures, in the presence of hydrogen, a hydrogenating-dehydrogenating function that makes it possible to convert the ethylbenzene in to a mixture of xylenes. Hydrogen is necessary to produce the naphthenic intermediate chemicals that yield xylenes after dehydrogenation.

The operating conditions of the isomerization are dictated by the conversion of ethylbenzene: temperature and partial pressure of hydrogen. The commercially available catalysts only ensure on the order of 40% of conversion per pass and require that a significant proportion of naphthenes be present in the loop. The applied temperature is increased to ensure the desired paraxylene production. Taking into account the compositions of the fresh feedstock and of the isomerate, it is necessary to treat the flow of fresh feedstock 3 to 5 times in the separation unit to produce about 0.85 times the flow of fresh feedstock in the form of paraxylene. The 10 to 20% of fresh feedstock that is not converted into paraxylene is found in the form of cracking and transalkylation products.

The second class of isomerization processes is known by the name dealkylating isomerization.

In this type of isomerization, ethylbenzene is converted into benzene and ethylene on catalysts with a zeolite ZSM5 base, while the xylenes are brought into thermodynamic equilibrium. Hydrogen is also needed here to hydrogenate into ethane the ethylene that is formed (to prevent realkylation) and to prevent the coking of the catalyst. The $H_2$/HC ratio, however, is considerably lower than that found in converting isomerization. In this case, co-production in the separation-isomerization loop of paraxylene (about 78%) and benzene (15%), with 7% of various losses, is ensured. Here again, the temperature conditions are still dictated by the fact that it is necessary to dealkylate the ethylbenzene.

In contrast, in industrial practice, ethylbenzene is the reaction intermediate chemical that makes it possible to obtain styrene by dehydrogenation. Ethylbenzene is always produced by alkylation of benzene with ethylbenzene. These alkylation units require a reactor with considerable recycling to be able to control the exothermicity of the reaction and, moreover, a number of distillations finally to separate gases, benzene, ethylbenzene, and di-, tri- and tetraethylbenzene.

Molecular sieves that can separate ethylbenzene from xylenes have been described effectively (U.S. Pat. No. 4,497,972, U.S. Pat. No. 5,433,560). Despite the respectable separation performance of these sieves, to our knowledge no commercial unit for separation of ethylbenzene in a simulated fluid bed has been built to date.

The prior art actually has always regarded the production of ethylbenzene as an isolated problem. If it is considered that the aromatic C8 feedstocks from which ethylbenzene is to be extracted contain at most 16%, a process for separating ethylbenzene, such as, for example EBEX®, is more expensive than a unit for alkylating benzene. This way of looking at things has quite often been reinforced by the fact that the locations where paraxylene and orthoxylene, on the one hand, and styrene, on the other, are produced are generally geographically separate: actually, the xylene production line is most often integrated into a refinery to keep from having to transport the aromatic $C_8$ petroleum fraction. In some cases, however, it is integrated into a plant for producing terephthalic acid or methyl terephthalate. By contrast, the ethylbenzene production line in generally integrated into a plant for producing styrene and polystyrene.

SUMMARY OF THE INVENTION

An object of the invention is to eliminate the drawbacks that are mentioned above.

Another object is the co-production of ethylbenzene and paraxylene.

An other object relates to the parallel production of essentially pure metaxylene and orthoxylene when the intent is not to maximize the production of paraxylene.

It has been observed that by combining a first adsorption step from which an ethylene-rich raffinate was drawn off with a second adsorption of this raffinate, from which a very ethylbenzene-poor fraction that contains orthoxylene and metaxylene that have been subjected to isomerization under favorable conditions would be drawn off, very good results under very economical conditions were observed.

More specifically, the invention relates to a process for co-production of paraxylene and ethylbenzene from an aromatic hydrocarbon feedstock (1) that contains isomers with 8 carbon atoms, in which in the presence of a first desorbent (6a), said feedstock is brought into contact with a zeolitic adsorbent in a first adsorption unit (2) in a simulated fluid bed; a first paraxylene-rich fraction (4) and a second paraxylene-poor and ethylbenzene-rich fraction ($R_1$) (3) are drawn off, characterized in that said second fraction ($R_1$) is brought into contact with a second suitable adsorbent in a second adsorption unit (8) in a simulated fluid bed in the presence of a second desorbent (12a); a third fraction (9) that comprises essentially pure ethylbenzene and a fourth orthoxylene-rich and metaxylene-rich fraction (10) that essentially no longer contains ethylbenzene are recovered; at least a portion of the fourth fraction is isomerized in an isomerization zone (14) in the presence of a suitable catalyst; an isomerate (16) is collected, and it is recycled to first adsorption unit (2).

The two adsorption units are generally used according to the simulated fluid bed technique.

According to an advantageous characteristic of the process, it is possible to define an additional chromatographic zone by using five zones instead of four, for example. Said zone is introduced downstream from the draw-off of second fraction ($R_1$) so as to collect the second fraction with a minimal first desorbent content, and downstream from said chromatographic zone another fraction $R_2$ (3a) is drawn off that is paraxylene-poor and orthoxylene-rich and metaxylene-rich but that essentially no longer contains ethylbenzene, and at least a portion of said fraction ($R_2$) is isomerized in isomerization zone (14).

The invention offers the following advantages:

The productivity of the separation process of paraxylene in the first adsorption unit is improved because the recycling of the isomerate that contains very little ethylbenzene in said unit leads to a reduction in the concentration of ethylbenzene of the adsorption feedstock, the productivity of the process for separation of ethylbenzene in the second adsorption unit is improved because of the absence of paraxylene in the feedstock of said unit, the absence of ethylbenzene in the isomerization feedstock makes it possible to operate the isomerization unit under much more favorable conditions than conventional units (a temperature of less than 20 to 30° C., low hydrogen pressure) and with better productivity (hourly volumetric flow rate greater than 20 to 50%). As a result, the production of undesirable by-products is avoided, unlike the conversion and dealkylating isomerizations of the prior art, finally, by producing at the output of the first adsorption unit two fractions (raffinates, for example), of which one that is very concentrated in ethylbenzene becomes the feedstock for the second adsorption unit, the size of said unit is reduced while its productivity is increased.

It is possible to distill the second $R_1$ ethylbenzene-containing fraction to eliminate at least a portion of the first desorbent and to recover the ethylbenzene-containing fraction that is introduced into the second adsorption unit for producing the essentially pure ethylbenzene and said fourth fraction that contains essentially metaxylene and orthoxylene.

This fourth fraction can be distilled so as to eliminate at least a portion of the second desorbent before being isomerized under mild conditions.

According to another characteristic of the process, when the draw-off of said raffinate that contains essentially metaxylene and orthoxylene is initiated in the first adsorption unit of fraction $R_2$, it is possible to distill this fraction so as to eliminate at least a portion of the first desorbent, before being isomerized. If it is necessary to do so, it may be advantageous to distill fourth fraction (13, 17) from which desorbent is removed so as to recover an essentially pure metaxylene distillate (19) and an essentially pure orthoxylene residue (20).

It becomes very advantageous to distill the first and second desorbents in the same distillation column when, quite clearly, the first and second desorbents are identical. This is particularly the case when the operation is carried out with toluene in the two adsorption units or with paradiethylbenzene.

It still remains possible to use a first desorbent in the first adsorption unit that is different from the second desorbent in the second unit.

It is possible to distill fraction ($R_2$) from which the first desorbent is removed so as to recover an essentially pure metaxylene distillate and an essentially pure orthoxylene residue. This distillation can advantageously be carried out in the same distillation column as the one that is used to treat the fourth orthoxylene and metaxylene fraction that is drawn off from the second adsorption unit.

According to a particularly advantageous characteristic, the first and second adsorption units use the principle of chromatography in a simulated fluid bed, in simulated countercurrent according to U.S. Pat. No. 2,985,589 or with simulated co-current according to U.S. Pat. Nos. 4,498,991 and 4,402,832. More specifically, it may be advantageous to operate the first unit under the following conditions:

Simulated countercurrent:

Temperature: 100° to 200° C.

Pressure: 2 to 30 bars (1 bar=$15^5$ Pa)

Desorbent to hydrocarbon-containing feedstock ratio: 1 to 2

Number of beds: 6 to 24

Desorbent: toluene or paradiethylbenzene

The adsorbents can be, for example, one of the ones described in U.S. Pat. Nos. 3,626,020 and 3,878,122.

More particularly, a zeolite X that is exchanged with barium and hydrated or a zeolite Y that is exchanged with potassium and barium is used. Toluene or para diethylbenzene will preferably be used as a desorbent. Of course, the desorbent will be selected based on the adsorbent.

The second adsorption unit for separating ethylbenzene from the mixture that comprises ethylbenzene, metaxylene, and orthoxylene can be operated under the following conditions:

Simulated countercurrent:

Number of beds: 6 to 24

Temperature: 100° to 200° C.

Pressure: 2 to 30 bars

Desorbent: toluene or paradiethylbenzene

Desorbent to feedstock ratio: 1 to 3

The zeolitic adsorbent of the second adsorption unit that feeds ethylbenzene can contain at least one element that is selected from the group of elements K, Rb, Cs, Ba, Ca, and Sr and optionally water. The conditions of this particular absorption are described in, for example, U.S. Pat. Nos. 5,453,560; 4,613,725; 4,108,915, 4,079,094 and 3,943,182.

Titanosilicate-containing adsorbents that preferably have a pore opening on the order of 8 Å, for example, such as those that are described in U.S. Pat. Nos. 5,244,650; 5,011,591 and 4,853,202, if the ethylbenzene/metaxylene selectivity is high, allow excellent separation and can provide excellent results.

The invention will be better understood based on the single FIGURE that diagrammatically illustrates the process.

A feedstock that is provided via a supply line 1 and comprises a mixture of paraxylene, orthoxylene, metaxylene, and ethylbenzene is introduced into a first adsorption unit 2. This unit comprises chromatographic columns that are filled with an adsorbent, a Ba-X zeolite, for example, and it operates according to the principle of a simulated fluid bed with countercurrent. Said unit comprises four chromatographic zones. A raffinate that consists essentially of orthoxylene and metaxylene and ethylbenzene and desorbent is recovered via a line 3. The desorbent which is toluene that is introduced via a line 6a makes it possible to desorb via a line 4 an extract that consists essentially of pure paraxylene and toluene that is distilled and recycled (not shown in the FIGURE).

The raffinate is sent via line 3 into a distillation column 5 which feeds a toluene distillate via a line 6 that is optionally recycled and a residue. The latter is introduced via a line 7 into a second adsorption unit 8 that operates as first unit 3, according to the principle of the simulated fluid bed with countercurrent. Said smaller second unit comprises columns that are filled with an adsorbent that contains, for example, titanosilicate. This unit comprises four main chromatographic zones. A raffinate that contains desorbent and metaxylene and orthoxylene is drawn off via a line 10 while an extract that contains essentially approximately pure ethylbenzene and desorbent is desorbed by the toluene that is introduced via a line 12a. This draw-off is carried out via a line 9 downstream from the line for introducing desorbent into unit 8.

The raffinate is sent into a distillation column 11 which feeds a toluene distillate via a line 12 and a residue of orthoxylene and metaxylene via a line 13. At least a portion of this residue can be introduced into a distillation unit 18 via a line 17. Said unit 18 makes it possible to recover an essentially pure metaxylene distillate via a line 19 and an essentially pure orthoxylene residue via a line 20. The other portion of the residue is sent into an isomerization unit which operates with or without hydrogen via a line 15 and which contains a suitable catalyst, for example mordenite or ZSM-5 with a known zeolite base, which is used under not very severe conditions of temperature and pressure since it does not contain ethylbenzene. The isomerate that is collected via a paraxylene-enriched line 16 essentially contains no ethylbenzene and is mixed at line 1 of the xylene feedstock of the first adsorption unit. The lightest hydrocarbons are evacuated from the isomerization zone via a line 21.

In the first adsorption unit, it is advantageous to define five chromatographic zones instead of four, as indicated above. A second raffinate which essentially does not contain ethylbenzene and does contain orthoxylene, metaxylene and a minimal quantity of desorbent is then drawn off upstream from the introduction of the desorbent (line 6a) and downstream from the raffinate (line 3), via a line 3a. Said line 3a is connected to line 10 for the introduction of the raffinate into distillation column 11, making it possible to eliminate the desorbent from the mixture of orthoxylene, metaxylene, and toluene.

The conditions of the isomerization stage that are described in U.S. Pat. No. 3,729,523, which is incorporated by reference, are generally as follows:

Presence of hydrogen not required.

Any catalyst for isomerization of xylenes and/or xylenes and ethylbenzene is suitable.

Catalyst which may or may not be zeolitic.

Liquid-phase or gas-phase process, preferably liquid-phase.

Temperature: 100 to 500° C., preferably 180° C. to 260° C.

Pressure: 1 bar to 140 bar, preferably 25 to 30 bar (1 bar=$10^5$ Pa).

VVH: from 0.5 to 20 $h^{-1}$, preferably 1 to 7 $h^{-1}$.

$H_2$/HC from 0 to 20 mol/mol, preferably 0 to 10.

Optionally injection of toluene at 5 to 30% by weight of the feedstock.

What is claimed is:

1. A process for co-production of paraxylene and ethylbenzene from an aromatic hydrocarbon feedstock (1) containing isomers with 8 carbon atoms, comprising contacting said feedstock in the presence of a first desorbent (6a) with a zeolitic adsorbent in a first adsorption unit (2) in a simulated fluid bed; drawing off a first paraxylene-rich fraction (4) and a second paraxylene-poor and ethylbenzene-rich fraction ($R_1$), represented by (3) bringing said second fraction ($R_1$) into contact with a second suitable adsorbent in a second adsorption unit (8) in a simulated fluid bed in the presence of a second desorbent (12a); recovering a third fraction (9) that comprises essentially pure ethylbenzene, and a fourth orthoxylene-rich and metaxylene-rich fraction (10) that essentially no longer contains ethylbenzene; isomerizing at least a portion of the fourth fraction in an isomerization zone (14) in the presence of a suitable catalyst; collecting an isomerate (16) and recycling said isomerate into first adsorption unit (2).

2. A process according to claim 1, wherein at least one additional chromatographic zone is added into first adsorption unit (2) downstream from the draw-off of second fraction ($R_1$) so as to collect the second fraction with a minimal first desorbent content, and another fraction ($R_2$), represented by (3a), is drawn off downstream from said chromatographic zone that is paraxylene-poor and orthoxylene-rich and metaxylene-rich but that essentially no longer contains ethylene, and at least a portion of said fraction ($R_2$) is isomerized in isomerization zone (14).

3. The process according to claim 1, further comprising distilling said second fraction $R_1$ to eliminate at least a portion of first desorbent (6a), recovering an ethylbenzene-rich fraction ($R_1$) (7) and introducing said ethylbenzene-rich fraction into second adsorption unit (8).

4. The process according to claim 1, further comprising distilling fourth fraction (10) so as to eliminate at least a portion of second desorbent (12) before isomerization.

5. The process according to claim 2, further comprising distilling said other fraction ($R_2$), represented by (3a), so as to eliminate at least a portion of the first desorbent before isomerization.

6. The process according to claim 1, further comprising distilling a portion of fourth fraction (17) from which the desorbent is removed so as to recover an essentially pure metaxylene distillate (19) and an essentially pure orthoxylene residue (20).

7. The process according to claim 5, wherein fourth fraction (10) and said other fraction ($R_2$) are distilled in same column (11).

8. The process according to claim 5, further comprising distilling a portion of fraction ($R_2$) from which the first desorbent is removed so as to recover an essentially pure metaxylene distillate and an essentially pure orthoxylene residue.

9. The process according to claim 8, further comprising distilling the fourth fraction and said other fraction from which desorbent has been removed in same column (18).

10. The process according to claim 1, wherein the second adsorbent contains titanosilicate.

* * * * *